United States Patent [19]

Ishida

[11] Patent Number: 5,125,920
[45] Date of Patent: Jun. 30, 1992

[54] BLOOD BAG AND BLOOD COLLECTING TUBE RECEIVING MEMBER TO BE ATTACHED TO BLOOD BAG

[75] Inventor: Noboru Ishida, Fujinomiya, Japan

[73] Assignee: Terumo Kabushiki Kaisha, Tokyo, Japan

[21] Appl. No.: 512,743

[22] Filed: Apr. 23, 1990

[30] Foreign Application Priority Data

Apr. 27, 1989 [JP] Japan ................... 1-109686

[51] Int. Cl.$^5$ ............................................. A61M 5/00
[52] U.S. Cl. ..................................... 604/410; 604/408
[58] Field of Search ........................................ 604/4–7, 604/408–416; 128/760–766; 248/311.2; 211/72, 74

[56] References Cited

U.S. PATENT DOCUMENTS

| 2,808,053 | 10/1957 | Morris . | |
|---|---|---|---|
| 3,127,892 | 4/1964 | Bellamy, Jr. et al. | 604/408 |
| 3,228,395 | 1/1966 | Gewecke | 604/408 X |
| 3,462,361 | 8/1969 | Greenwalt et al. | 604/7 |
| 3,467,095 | 9/1962 | Ross | 604/6 |
| 3,494,351 | 2/1970 | Horn | 128/762 |
| 4,103,685 | 8/1978 | Lupien et al. | 604/6 |
| 4,410,026 | 10/1983 | Boggs et al. | 604/408 X |
| 4,425,113 | 1/1984 | Bilstad | 604/6 |
| 4,508,236 | 4/1985 | Keilman . | |
| 4,846,795 | 7/1989 | Minagawa . | |
| 4,892,537 | 1/1969 | Carmen et al. | 604/408 |

FOREIGN PATENT DOCUMENTS 2548905 3/1985 France .
916457 1/1963 United Kingdom .

Primary Examiner—Robert A. Hafer
Assistant Examiner—Kerry Owens
Attorney, Agent, or Firm—Frishauf, Holtz, Goodman & Woodward

[57] ABSTRACT

A blood bag of the present invention comprises a blood collection container; a tube communicating with the blood collection container and provided with a blood collecting needle at its distal end; and a blood collecting tube receiving member attached to the tube detachably or movably along the tube. Before labels are stuck on, a blood collecting tube into which blood has been collected from this blood bag is not confused with another blood collecting tube into which blood has been collected from another blood bag, or after labels are stuck on, blood is not collected from another blood bag into a blood collecting tube in which has been stuck a label having the same as serial number as a label stuck on this blood bag, so as to avoid a danger that blood having an infectious disease is transfused for mistaking it for safe blood.

5 Claims, 4 Drawing Sheets

FIG. 6
FIG. 7
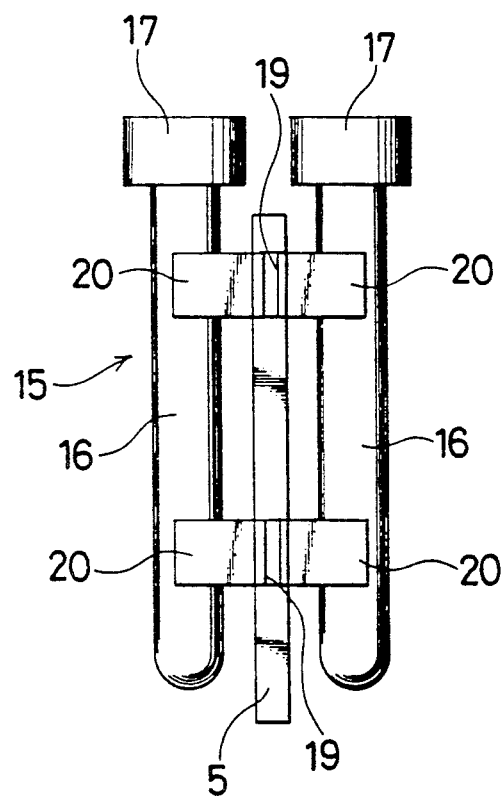
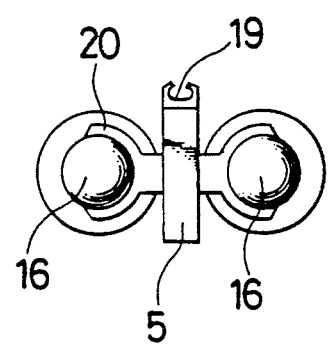

BLOOD BAG AND BLOOD COLLECTING TUBE RECEIVING MEMBER TO BE ATTACHED TO BLOOD BAG

BACKGROUND OF THE INVENTION

This invention relates to a blood bag for use in collecting blood and a blood collecting tube receiving member to be attached to the blood bag.

Blood collection is generally done by using a blood bag. Collected blood is transfused to a patient as it is (all components of blood). Alternatively, only the necessary components separated from the blood by centrifugation are transfused. Collected blood is examined in order to avoid infection of an infectious disease, for example, post-transfusion hepatitis such as hepatitis B and non-A non-B hepatitis, AIDS (acquired immunodeficiency syndrome), venereal disease, etc. For this examination, after collecting blood into the blood bag, the blood collecting needle of the blood bag system is withdrawn from the donor and then pierces a sealing member (rubber plug) of a blood collecting tube the interior of which is depressurized to collect a sample of the blood in the blood bag. The sample of blood is subjected to necessary tests.

On the blood collecting tube is a label having the same serial number as a label stuck on the blood bag so as to check the blood in the blood collecting tube being the same as that in the blood bag. In many cases, however, plural blood collection works using blood bags are parallelly done, for example, in a car for blood donation. In such a car for blood donation, there are confusedly present plural blood collecting tubes containing different blood. As a result, there is a possibility that labels are erroneously stuck on the blood collecting tubes. Besides, in the case that labels are previously stuck on the blood collecting tubes prior to blood collection works, there is a possibility that blood is collected into a blood collecting tube from a wrong blood bag, that is, a blood bag provided with the label having a different serial number from that of the label on the blood collecting tube into which blood is collected. Such erroneous affixation of labels or confusion of blood bags is dangerous because blood having an infectious disease may be transfused for mistaking it for safe blood.

SUMMARY OF THE INVENTION

Accordingly, it is an object of the present invention to provide a blood bag wherein, before lables are stuck on, a blood collecting tube into which blood has been collected from this blood bag is not confused with another blood collecting tube into which blood has been collected from another blood bag, or after labels are stuck on, blood is not collected from another blood bag into a blood collecting tube which has a label having the same serial number as a label stuck on this blood bag, so as to avoid the danger that blood having an infectious disease is transfused for mistaking it for safe blood.

The above object is attained by a blood bag comprising a blood collection container; a tube communicating with the blood collection container and provided with a blood collecting needle at its distal end; and a blood collecting tube receiving member attached to the tube detachably or movably along the tube.

The above object is attained by a blood bag comprising a blood collection container; a first tube communicating with the blood collection container and provided with a blood collecting needle at its distal end; a blood components container; a second tube connecting the blood collection container to the blood components container; and a blood collecting tube receiving member attached to the first or second tube detachably or movably along the tube.

The above object is attained by a blood collecting tube receiving member to be attached to a blood bag, comprising a blood collecting tube mounting portion for mounting a blood collecting tube detachably, and an attachment portion to the blood bag.

BRIEF DESCRIPTION OF THE DRAWINGS

FIG. 6 is a front elevation of the blood collecting tube receiving member of one embodiment of the present invention by which blood collecting tubes are received; and FIG. 7 is a bottom view of the blood collecting tube receiving member of FIG. 6.

DETAILED DESCRIPTION OF THE PREFERRED EMBODIMENTS

Figure 1:
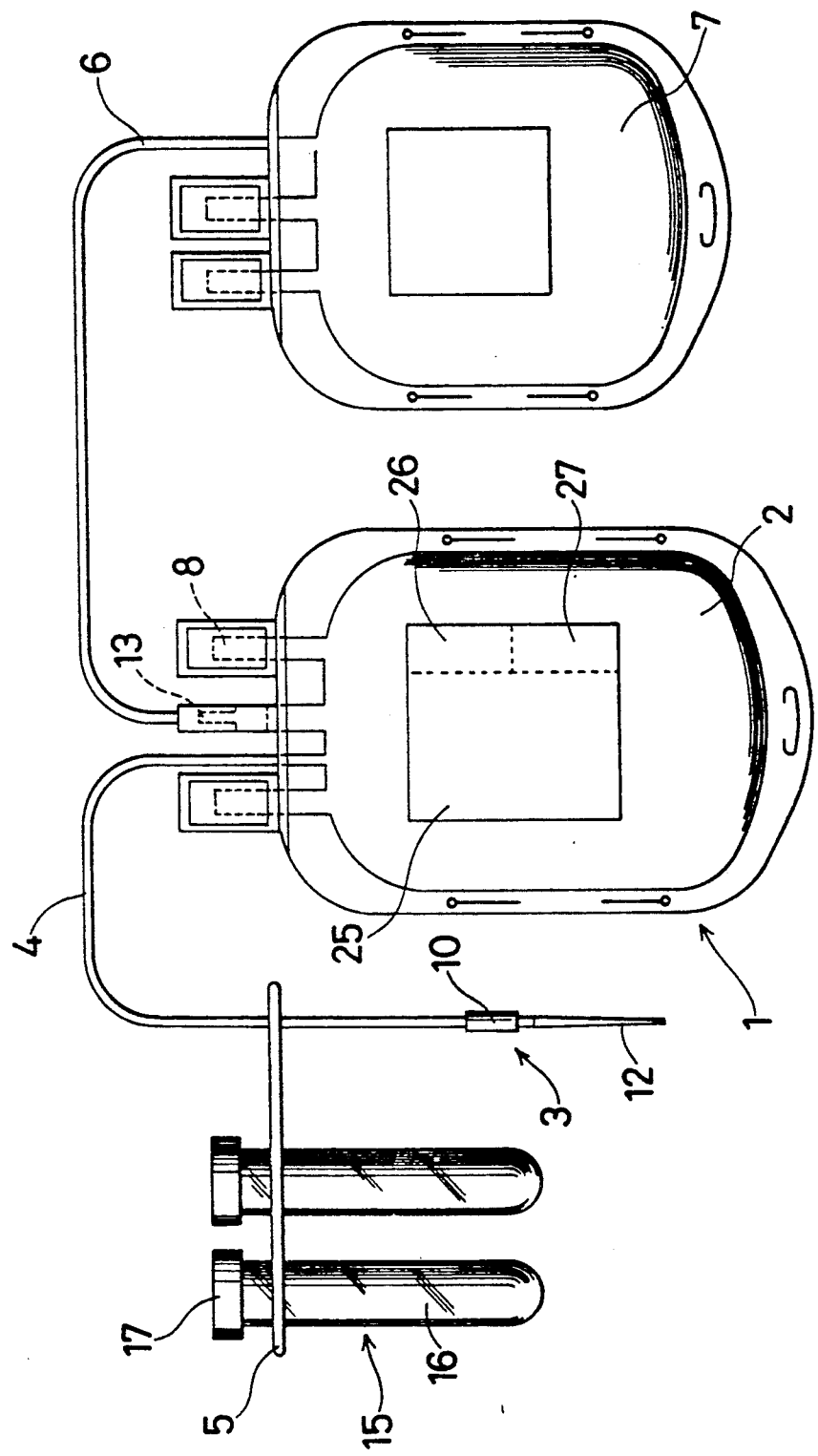
FIG. 1 is a view of one embodiment of the blood bag of the present invention.

The blood bag of the present invention will be described with reference to an embodiment shown in the drawings.

The blood bag 1 of the present invention comprising a blood collection container 2; a tube 4 communicating with the blood collection container 2 and provided with a blood collecting needle 3 at its distal end; and a blood collecting tube receiving member 5 attached to the tube 4 detachably or movably along the tube 4.

The blood bag of the present invention will be described with reference to an embodiment shown in FIGS. 1 and 2.

The blood collection container 2 of the blood bag 1 is generally called a master bag, in which anticoagulant is contained and which is capable of receiving blood. In this example, the blood collection container 2 is made of flexible synthetic resin into a bag. Anticoagulant liquid contained therein may be well-known ACD liquid or CPD liquid. The blood collection container 2 is made of flexible synthetic resin having some extent of oxygen-permeability such as flexible vinyl chloride resin and silicone resin because it is used as a red blood cell reservoir after blood collection. A label 25 is affixed on the surface of the blood collection container 2. The label 25 includes labels 26 and 27 to be stuck on blood collecting tubes.

A first tube 4 is connected to the blood collection container 2 so as to be in fluid communication with the interior of the blood collection container 2. The first tube 4 is made of flexible synthetic resin such as flexible vinyl chloride resin and silicone resin like the the blood collection container 2. A blood collecting needle 3 which is stabbed in a donor is attached to the distal end of the tube 4. The blood collecting needle 3 comprises a hub 10 mounted to the distal end of the first tube 4 in a liquid-tight manner, a puncture needle mounted to the hub 10, and a protector 12 for protecting the puncture needle 11. The protector 12 is detachably attached to the hub 10 in a liquid-tight manner so as to prevent anticoagulant in the blood collection container 2 from flowing out.

In the blood bag 1 of this example, a second tube 6 is connected to the blood collection container 2. A blood component collection container 7 is connected to the other end of the second tube 6. The blood component collection container 7 is generally called a slave bag. The blood bag is set in a centrifugal machine after blood collection to separate blood collected in the blood collection container 2 into, for example, plasma component and blood cell component. The blood component collection container 7 is used for collecting the component separated into the upper part of the blood (for example, plasma component).

The second tube 6 is provided with a breakable communicating member 13 to prevent anticoagulant in the blood collection container 2 from flowing in the blood component collection container 7 before blood collection. Each of the blood collection container 2 and blood component collection container 7 is provided with a blood outlet 8. The blood outlet 8 is closed and allows a connector of a transfusion set (not shown) to penetrate.

Figure 2:
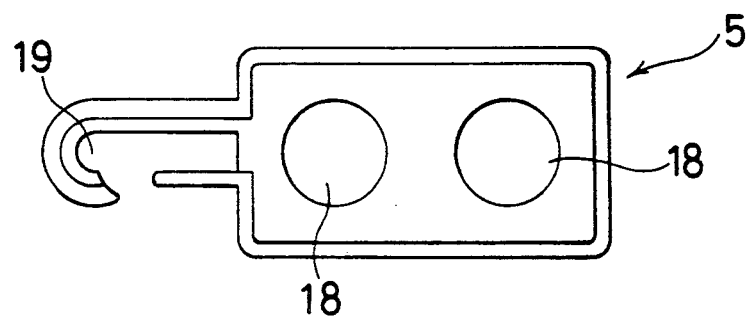
FIG. 2 is a plan view of the blood collecting tube receiving member used in the blood bag shown in FIG. 1.

In the blood bag 1 of this example, a blood collecting tube receiving member 5 is attached to the first tube 4 detachably and movably along the tube 4 as shown in FIGS. 1 and 2. The blood collecting tube receiving member 5 may be attached to the first tube either detachably or movably unlike this example.

It is preferable that the blood collecting tube receiving member 5 is capable of receiving more than two blood collecting tubes 15. The reason is that the same blood is generally collected in more than two blood collecting tubes according to different blood collection manners in blood tests.

The blood collecting tube receiving member 5 of the example shown in FIGS. 1 and 2 has holes 18 each of which allows the bottomed tube 16 of a blood collecting tube 15 to be inserted therein and is smaller than the sealing member 17 of the blood collecting tube 15. The blood collecting tube receiving member 5 also has an attachment portion 19 to the first tube 4. The hole 18 preferably has the inner diameter substantially equal to the outer diameter of the bottomed tube 16 so as to hold the blood collecting tube 15 in slidable contact with the outer surface of the bottomed tube 16. The blood collecting tube receiving member 5 is attached to the tube 4 detachably and movably along the tube 4. The blood collecting tube receiving member 5 can be made of a material having some extent of rigidity, for example, polypropylene, polyethylene, vinyl chloride resin or polystyrene, facilitating manipulation.

Figure 3:
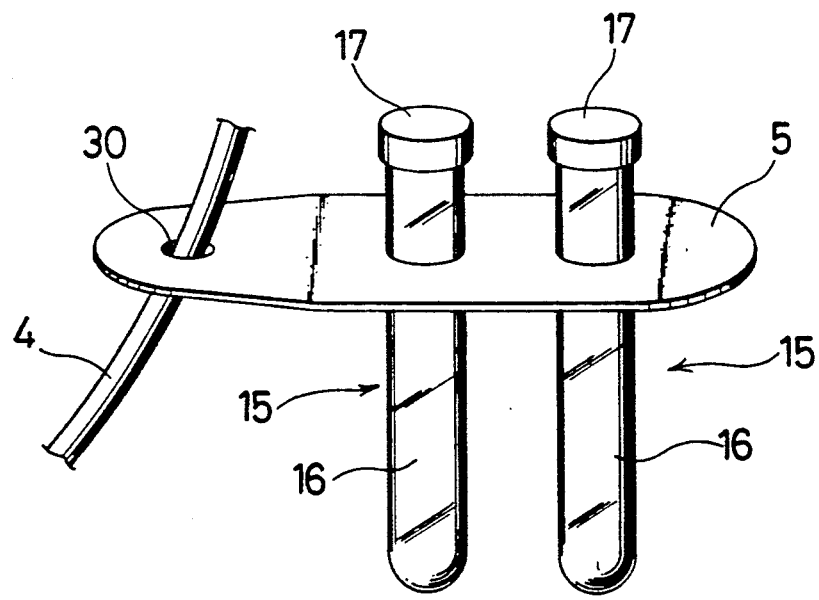
FIG. 3 is a view near the blood collecting tube receiving member of another embodiment of the blood bag of the present invention.

The blood collecting tube receiving member 5 is not limited to this example but may have a hole 30 for the tube 4 passing through so that the blood collecting tube receiving member 5 is attached to the tube 4 not detachably but movably along the tube 4 as shown in FIG. 3. In the case of the blood collecting tube receiving member 5 undetachable from the tube 4 like this example, the blood collecting tube receiving member 5 is preferably made of a material not injuring the blood bag upon centrifugation of the blood bag 1, for example, elastomer such as flexible vinyl chloride resin and polyurethane, or rubber material such as silicone rubber and latex rubber.

Figure 4:
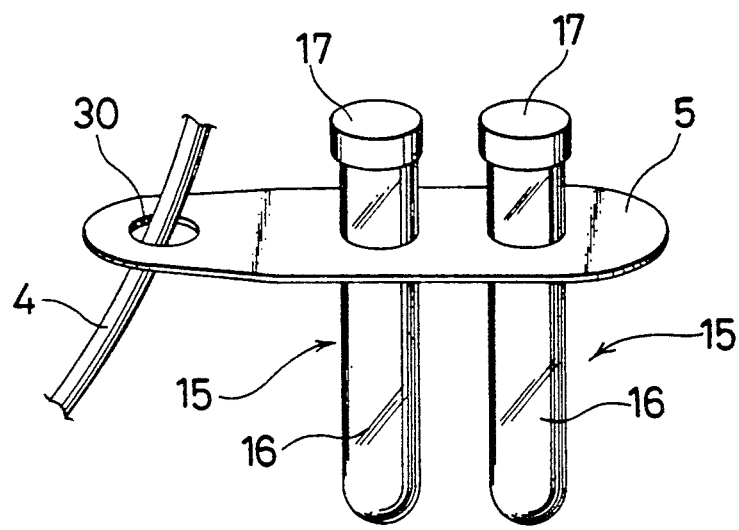
FIG. 4 is a view near the blood collecting tube receiving member of another embodiment of the blood bag of the present invention.

The blood collecting tube receiving member 5 may have such a large hole 30 as to allow the blood collecting needle to pass through as shown in FIG. 4 though the blood collecting tube receiving member 5 has a similar shape to that of FIG. 3. Thereby, the blood collecting tube receiving member 5 is detachable from the tube 4.

Figure 5:
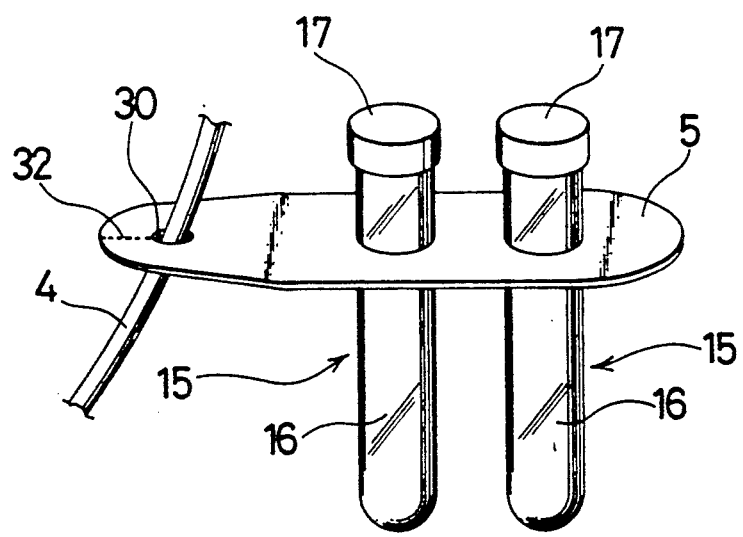
FIG. 5 is a view near the blood collecting tube receiving member of another embodiment of the blood bag of the present invention.

Alternatively, the blood collecting tube receiving member 5 may have a weak portion 32 extending from the hole 30 to the outer edge of the blood collecting tube receiving member 5 as shown in FIG. 5 though the blood collecting tube receiving member 5 has a similar shape to that of FIG. 3. Thereby, when the blood collecting tube receiving member 5 is pulled, it is cut at the weak portion 32 so as to be detached from the tube 4.

The tube 4 of the blood bag 1 is subjected to a heat seal operation after blood collection. In the heat seal operation, blood in the tube 4 is divided into four to eight sections between the portion of the tube 4 at which the blood collecting needle is attached and the vicinity of the blood collection container in order that the blood is used in cross matching tests. In this case, the blood collecting tube receiving member 5 does not obstruct the heat seal operation because it is attached to the tube 4 detachably or movably along the tube 4.

The blood collecting tube receiving member 5 may be attached to the second tube 6 connecting the blood collection container 2 to the blood component collection container 7.

In this manner, by attaching the blood collecting tube receiving member 5 to the first or second tube 4 or 6 detachably or movably along the tube, the tube position easy for blood collection into the blood collecting tube 15 can optionally be selected, facilitating the blood collection work.

The blood collecting tube receiving member 5 may be constructed as shown in FIGS. 6 and 7. FIG. 6 shows a front elevation of the blood collecting tube receiving member 5 which receives blood collecting tubes. FIG. 7 is a bottom view of FIG. 6. The blood collecting tube receiving member 5 of this example has an attachment portion 19 for detachably holding the first or second tube 4 or 6, and two pairs of fixing portions 20 for blood collecting tubes. This blood collecting tube receiving member 5 is easy of manipulation because it can be had in the state that two blood collecting tubes 15 are fixed to it as shown in FIG. 6 and it is detached from the tube. Because the blood collecting tube receiving member 5 can be attached to any portion of the tube, the tube position easy for blood collection into the blood collecting tubes 15 can optionally be selected. It is thus possible that the blood collecting tube receiving member 5 previously fixing plural blood collecting tubes 15 is provided, attached to an optional position of the tube 4, and after blood collection, detached from the tube 4 together with the blood collecting tubes 15.

In a preferred form of the blood collecting tube receiving member 5, it is possible to collect blood into the blood collecting tube, stick labels on the blood collecting tubes, and check the serial numbers of labels of the blood collecting tubes and blood bag in the state that the blood collecting tube receiving member 5 is attached to the blood bag 1. The order of steps of collecting blood into the blood collecting tube and affixing the labels is optional. All of the examples described above meet these requirments. Although the blood collecting tube receiving member 5 is attached to the tube in the examples described above, the blood collecting tube receiving member 5 may be attached to, for example, the hub or protector of the blood collecting needle 3.

The operation of the blood bag of the present invention will be described with reference to the embodiment shown in FIGS. 1 and 2.

First, the blood collecting tube receiving member 5 is attached to the blood bag 1. A blood collecting tube 15 is inserted in and fixed to each of the holes 18 constituting the blood collecting tube fixing portion of the blood collecting tube receiving member 5. Next, labels 26 and 27 for blood collecting tubes which are parts of the label 25 stuck on the blood collection container 2 are peeled off and then stuck on the surfaces of the bottomed tubes 16 of the blood collecting tubes 15, respectively. At this time, it is checked that the serial number of the labels of the blood collecting tubes 15 corresponds to that of the label of the blood collection container 2. Subsequently, the blood collecting needle 3 is stabbed into a donor to collect blood into the blood collection container 2. After the blood collecting needle 3 is withdrawn from the donor, it is made to pierce the sealing member 17 of one of the blood collecting tubes 15 to collect a part of the blood of the blood bag into the blood collecting tube 15. The operation of collecting blood from the blood bag is repeated twice. After this, the blood collecting tubes 15 are separated from the blood collecting tube receiving member 5 and necessary blood tests are carried out. At this time, if the blood collecting tube receiving member 5 is detachable from the tube 4, it may be detached together with the blood collecting tubes 15. The labels 26 and 27 may be stuck on the blood collecting tubes 15 after blood collection into the blood collecting tubes 15.

The blood bag of the present invention comprises a blood collection container; a tube communicating with the blood collection container and provided with a blood collecting needle at its distal end; and a blood collecting tube receiving member attached to the tube detachably or movably along the tube. Therefore, it is advantageous because, before labels are stuck on, a blood collecting tube into which blood has been collected from this blood bag is not confused with another blood collecting tube into which blood has been collected from another blood bag, or after labels are affixed, blood is not collected from another blood bag into a blood collecting tube on which has been affixed a label having the same serial number as a label on this blood bag, so as to avoid a danger that blood having an infectious disease is transfused by mistaking it for safe blood.

The blood bag of the present invention comprises a blood collection container; a first tube communicating with the blood collection container and provided with a blood collecting needle at its distal end; a blood components container; a second tube connecting the blood collection container to the blood components container; and a blood collecting tube receiving member attached to the first or second tube detachably or movably along the tube. Therefore, it is advantageous because, before labels are stuck on, a blood collecting tube into which blood has been collected from this blood bag is not confused with another blood collecting tube into which blood has been collected from another blood bag, or after labels are stuck on, blood is not collected from another blood bag into a blood collecting tube on which has been stuck a label having the same serial number as a label stuck on this blood bag, so as to avoid the danger that blood having an infectious disease is transfused by mistaking it for safe blood.

The blood collecting tube receiving member of the present invention to be attached to a blood bag, comprises a blood collecting tube mounting portion for mounting a blood collecting tube detachably, and an attachment portion to the blood bag. Therefore, it is advantageous for the same reason as the above blood bag.

We claim:
1. A blood bag, comprising:
a blood collection container;
a first tube communicating with said blood collection container, said tube having a distal end;
a blood collecting needle mounted at the distal end of said tube;
a blood components container;
a second tube connecting said blood collection container to said blood components container; and
a detachable blood collecting tube receiving member attached to said first tube.
2. A blood bag system, comprising:
a blood collection container;
an elongated tube communicating with said blood collection container, said elongated tube having a distal end;
a blood collecting needle mounted at the distal end of said elongated tube; and
a blood collecting tube receiving member movably attached to said elongated tube to enable movement thereof along said elongated tube.
3. A blood bag system according to claim 2, comprising a plurality of blood collecting tubes, and wherein said blood collecting tube receiving member comprises means for retaining said plurality of blood collecting tubes.
4. A blood bag system, comprising:
a blood collecting container;
a first tube communicating with said blood collecting container, said first tube having a distal end;
a blood collecting needle mounted at said distal end of said first tube;
a blood components container;
a second tube connecting said blood collection container to said blood components container; and
a blood collecting tube receiving member movably attached to said first tube to be movable along said first tube.
5. A blood bag system according to claim 4, comprising a plurality of blood collecting tubes wherein said blood collecting tube receiving member comprises means for holding said plurality of blood collecting tubes.

* * * * *